(12) United States Patent
Rottenberg et al.

(10) Patent No.: US 10,524,824 B2
(45) Date of Patent: Jan. 7, 2020

(54) ACTIVE OBSTRUCTION CROSSING DEVICE

(71) Applicant: Upstream Peripheral Technologies Ltd., Caesarea (IL)

(72) Inventors: Dan Rottenberg, Haifa (IL); Yosi Pesis, Pardes Hana (IL)

(73) Assignee: Upstream Peripheral Technologies Ltd., Caesarea Business Park (IL)

( * ) Notice: Subject to any disclaimer, the term of this patent is extended or adjusted under 35 U.S.C. 154(b) by 73 days.

(21) Appl. No.: 15/110,746

(22) PCT Filed: Jan. 8, 2015

(86) PCT No.: PCT/US2015/010553
§ 371 (c)(1),
(2) Date: Jul. 10, 2016

(87) PCT Pub. No.: WO2015/105930
PCT Pub. Date: Jul. 16, 2015

(65) Prior Publication Data
US 2016/0331394 A1 Nov. 17, 2016

Related U.S. Application Data

(60) Provisional application No. 61/926,329, filed on Jan. 12, 2014.

(51) Int. Cl.
*A61B 17/22* (2006.01)
*A61B 17/3207* (2006.01)
(52) U.S. Cl.
CPC .......... *A61B 17/3207* (2013.01); *A61B 17/22* (2013.01); *A61B 2017/22094* (2013.01)

(58) Field of Classification Search
CPC .... A61B 17/22012; A61B 2017/22094; A61B 17/22004; A61B 17/22; A61B 2017/22042; A61B 2017/22044; A61B 17/3207
USPC ......................................... 606/159, 171, 185
See application file for complete search history.

(56) References Cited

U.S. PATENT DOCUMENTS 4,154,239 A * 5/1979 Turley ............... A61M 37/0069
604/61
4,559,041 A * 12/1985 Razi ................... A61B 17/3415
128/207.29
5,123,909 A 6/1992 Leveen
(Continued)

FOREIGN PATENT DOCUMENTS

EP 0623360 11/1994
FR 2645009 10/1990
(Continued)

OTHER PUBLICATIONS

PCT Written Opinion PCT/US2015/010553, dated Mar. 20, 2015.

*Primary Examiner* — Kathleen S Holwerda
(74) *Attorney, Agent, or Firm* — Dekel Patent Ltd.; David Klein

(57) ABSTRACT

Devices and methods are described for penetrating hard plaque that partially or completely occludes blood vessels and disturbs blood flow through the blood vessel. The device includes a distal pre-loaded spring that can store energy and release it as impact at the device distal tip, in order to penetrate or break through hard plaque that is blocking blood path in blood vessels.

10 Claims, 8 Drawing Sheets

(56) References Cited

U.S. PATENT DOCUMENTS

| | | | | |
|---|---|---|---|---|
| 5,449,369 A | * | 9/1995 | Imran | A61B 17/2202 600/585 |
| 7,066,873 B2 | * | 6/2006 | Hughett | A61N 5/1007 600/7 |
| 8,337,424 B2 | * | 12/2012 | Palmer | A61M 25/09041 600/104 |
| 2011/0275990 A1 | * | 11/2011 | Besser | A61B 17/22032 604/99.01 |
| 2012/0165850 A1 | * | 6/2012 | Deckard | A61B 17/22012 606/185 |
| 2012/0330335 A1 | * | 12/2012 | Shekalim | A61B 17/22012 606/159 |

FOREIGN PATENT DOCUMENTS

| | | |
|---|---|---|
| WO | 88/02243 | 4/1988 |
| WO | 2011/005971 | 1/2011 |

\* cited by examiner

ACTIVE OBSTRUCTION CROSSING DEVICE

FIELD OF THE INVENTION

The present invention relates generally to devices and methods for penetrating hard plaque that partially or completely occludes blood vessels and disturbs blood flow through the blood vessel.

BACKGROUND OF THE INVENTION

Atherosclerosis is a complex, progressive and degenerative condition resulting in the build-up of cholesterol and other obstructive materials, known as plaque, on the walls of the arteries. The accumulation of plaque narrows the interior or lumen of arteries, thereby reducing blood flow. Plaque occurs in the arteries in several different forms and may be located in many different anatomies throughout the arterial system. Plaque varies in composition, with portions that are hard and brittle, referred to as calcified. plaque, and other portions that are fatty or fibrous. Over time atheromatous deposits can become large enough to reduce or totally occlude blood flow through the vessels, leading to symptoms of low blood flow, such as pain in the legs (during walking or at rest), skin ulcer, angina, and other symptoms.

Chronic Total Occlusions (CTOs), are usually hard calcified plaque blocking all blood paths through the vessel, and are found in a large percentage of the patients. To treat this disease and improve or resolve these symptoms it is desirable to restore or improve blood flow through the vessel.

Various means are used to restore or improve blood flow through atheromatous vessels. The atheroma deposits can be displaced by diametrically expanding the vessel by inflating balloons, expanding stents, and other methods.

The plaque can be pulverized using lasers and other methods however pulverization alone of atheromatous material may allow micro-emboli to flow downstream and lodge in distal vascular beds, further compromising blood flow to the tissue affected by the disease.

Many types of atherectomy catheter devices have been proposed, including catheters with rotating burrs, lasers to photo-dissolve tissue, catheters with ultrasonic vibration mechanisms, and catheters which use balloons or other positioning features to position the cutter adjacent material to be removed.

Most of current CTO crossing devices or atherectomy devices are led over standard guidewires, preventing them from exit the vessel walls while moving forward removing the plaque. This means that a thin guidewire, usually between 0.014" to 0.035" in diameter, must first cross the total occlusion. Special crossing guidewires are available today, so-called CTO wires, designed especially to cross plaque material, including calcified and hard plaque material.

Few crossing or atherectomy devices do not ride over a guidewire, but then they must have some sort of imaging system and/or controlled maneuverability and bending capabilities, to keep inside the blood vessel lumen, preventing vessel perforation. Such mechanism or imaging systems significantly increase their cost.

The CTO proximal cap is usually the harder part of the occlusion, and if the guidewire or crossing device can penetrate the CTO proximal cap, they usually can cross the whole length of the CTO.

Still in about 20% of the peripheral CTO patients, the CTO proximal cap is too hard and impossible to penetrate for any guidewire and/or crossing device. The only options for the physician in such cases is to cross the CTO sub-intimally, probably using expensive lumen reentry devices, or use the relative complex retrograde technique and cross the occlusion from the distal cap, which is usually softer then the proximal cap.

SUMMARY OF THE INVENTION

The present invention relates to a device and method for penetrating hard plaque that partially or completely occludes blood vessels and disturbs blood flow through the blood vessel. The device disclosed includes a distal pre-loaded spring. The distal biasing device located at the device distal tip can store energy and release it as an impact force in order to penetrate or break through hard plaque blocking blood path in blood vessels. The distal biasing device is preferably a pre-loaded spring, allowing storage of high energy level for impact.

The device of the invention is designed for percutaneous insertion into the blood vessels over standard guidewire. The device is preferably used in cases where the plaque is too hard for a guidewire to penetrate, and there is a need for the crossing-device to penetrate the occlusion proximal hard cap, and/or the whole occlusion length.

If desired, the device of the invention can be used to break the hard proximal cap of the CTO, and then the rest of the occlusion is penetrated with CTO guidewires. In such cases standard balloon angioplasty and possibly stents are used to open the occlusion.

In cases where the guidewire cannot cross the rest of the occlusion by itself, the crossing device of the invention and the guidewire can both be further advanced through the occlusion, while providing additional impacts on the plaque in order to further penetrate it.

A centering balloon may be added to the crossing device of the invention, positioned just proximally to the device distal tip. The balloon is preferably slightly smaller than the blood vessel lumen so as not to disturb the device advancement through the occlusion, but rather just to aim the device tip to the center of the occlusion before applying the impact.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
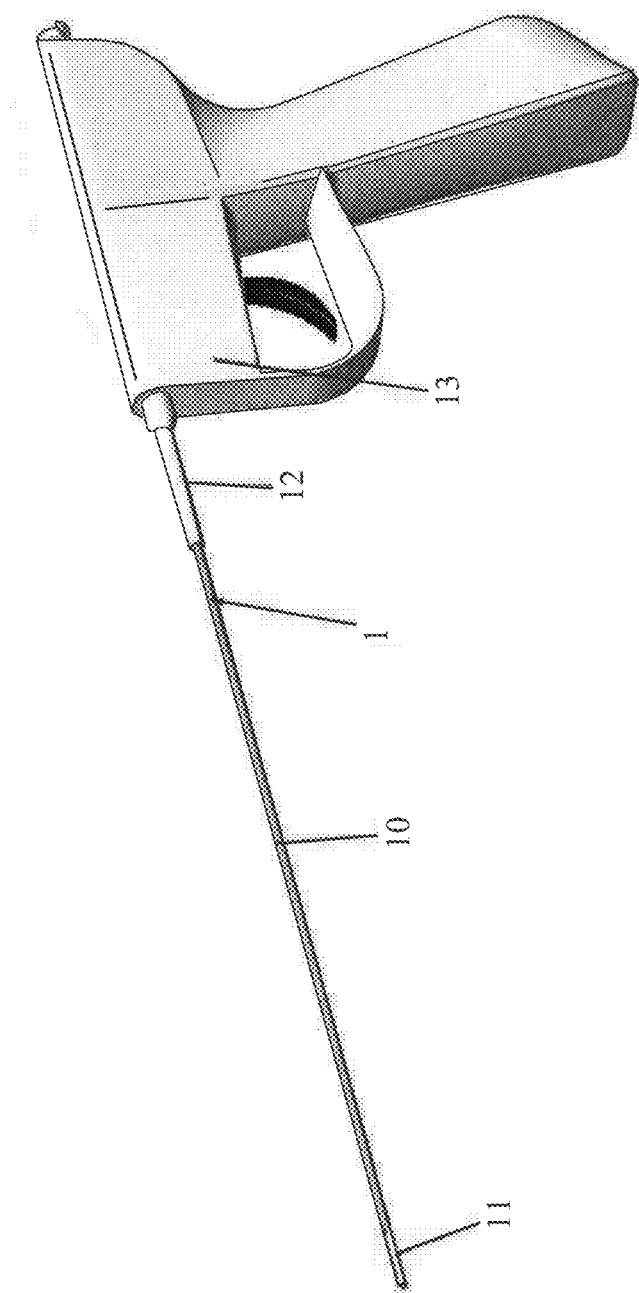
FIG. 1 is a schematic illustration of an embodiment of the crossing device of the invention.

As seen in FIG. 1, a device 1 is provided for penetrating hard plaque, which partially or completely occlude blood vessels and reduces or eliminates blood flow through the vessel. Device 1 includes a main body long shaft 10 having a distal portion 11 and a proximal portion 12. A handle 13 with an activating mechanism is attached to proximal shaft portion 12.

Figure 3:
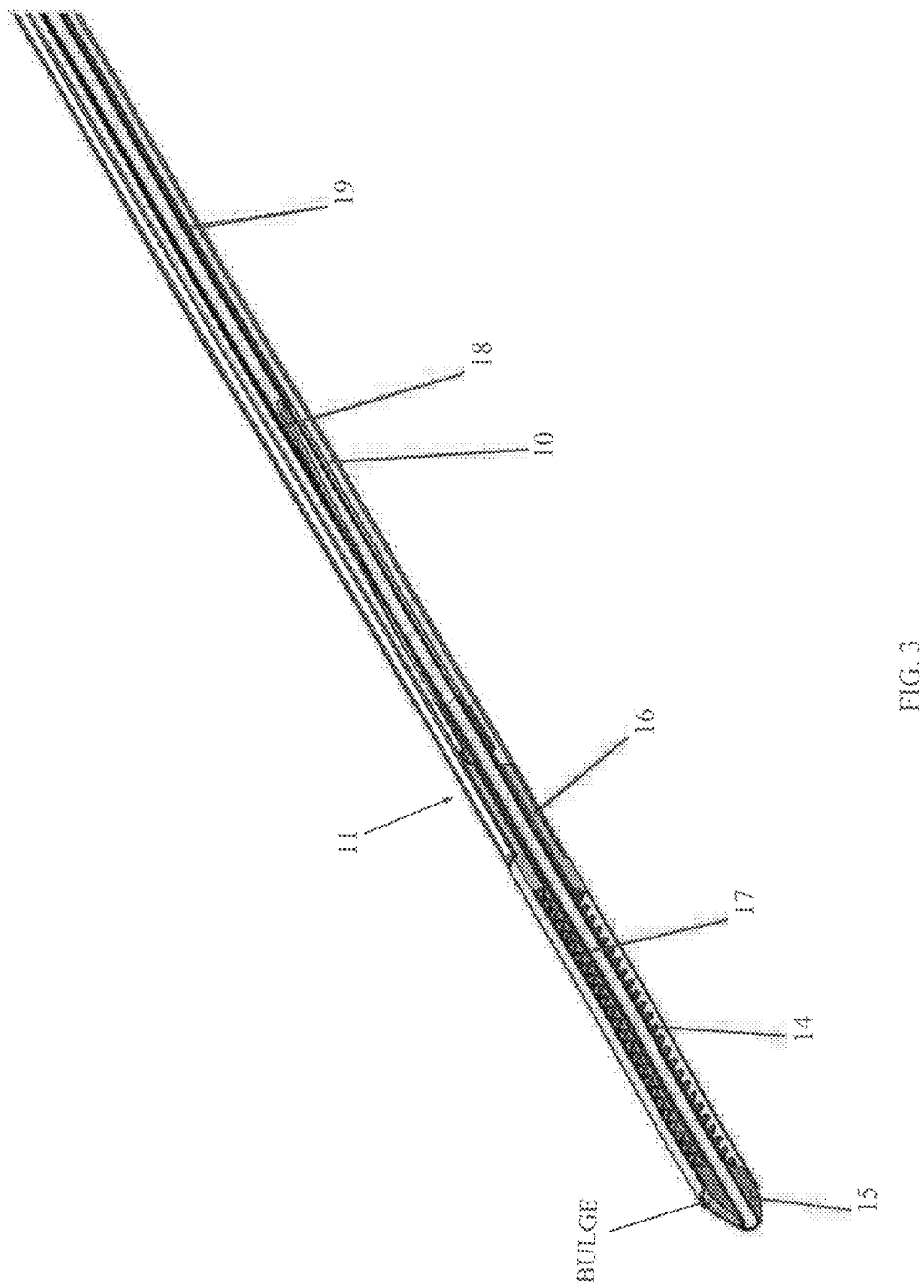
FIG. 3 is a partial schematic cross-section illustration of an embodiment of the distal section of the crossing device of the invention.

As seen in FIG. 3, distal shaft portion 11 ends in an impactor 15 (which may be cone-shaped), which is attached to a distal biasing device 14, such as a coil spring or leaf spring and the like, the terms being used interchangeably. Distal biasing device 14 can store or accumulate energy and release it as an impact force through the distal tip of device 1 in order to penetrate or break through hard plaque that blocks blood path in blood vessels.

Figure 2:
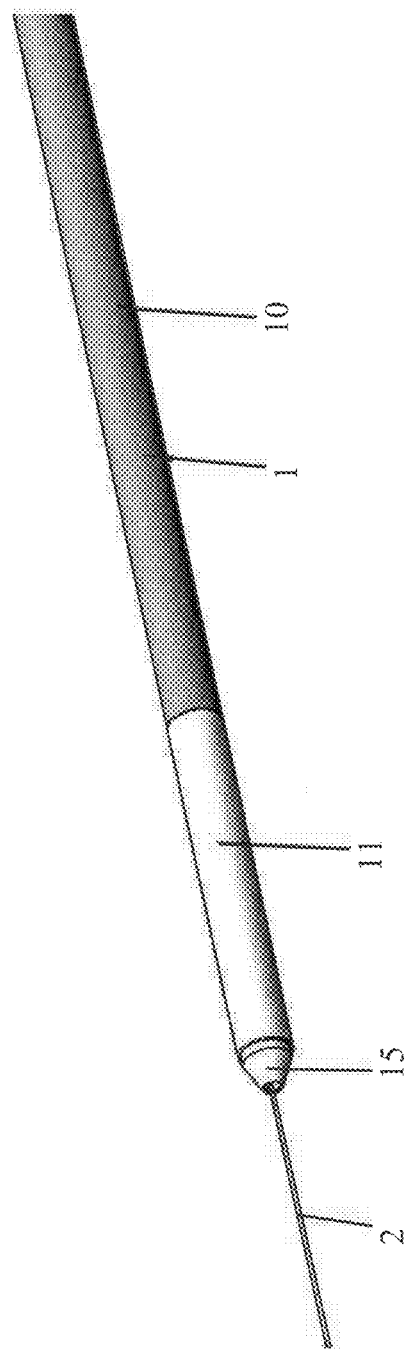
FIG. 2 is a schematic illustration of an embodiment of the distal section of the crossing device of the invention.
Figure 4B:
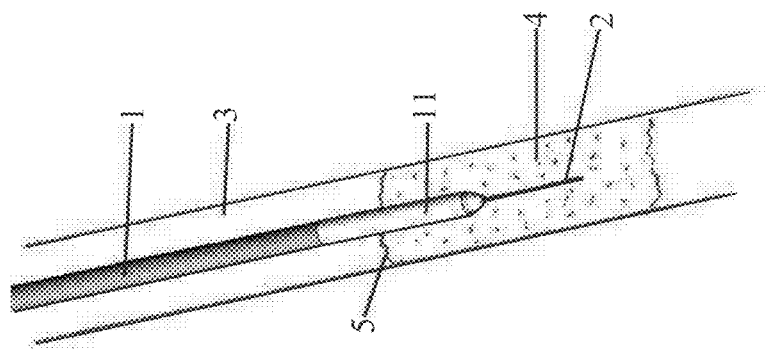
FIGS. 4A and 4B are schematic illustrations of an embodiment of the distal section of the crossing device of the invention inside blood vessel with total occlusion.
Figure 4A:
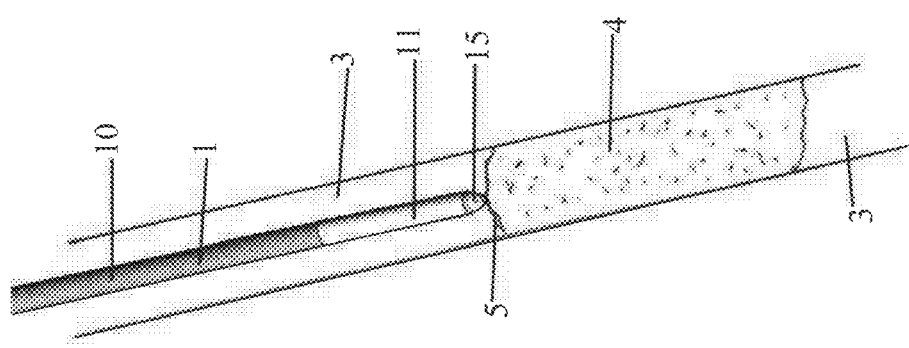

Reference is now made to FIGS. 4A-4B. Device 1 is designed for percutaneous insertion into a blood vessel 3 over a guidewire 2 (also seen in FIG. 2). Device 1 is preferably used in cases where plaque 4 is too hard for a guidewire to penetrate, and there is a need for a crossing-device to penetrate an occlusion proximal hard cap 5, and/or the whole length of the occlusion 4.

Device 1 can be used to break the hard proximal cap 5 of a CTO, and then the rest of the occlusion 4 can be penetrated with the CTO guidewire 2. In such cases, standard balloon angioplasty and possibly stents may be used to open the occlusion, following the guidewire.

In cases where guidewire 2 cannot cross the rest of the occlusion 4 by itself, the crossing device 1 of the invention and the guidewire 2 can be further advanced through the occlusion 4, while providing additional multiple impacts on the plaque in order to further penetrate it.

Reference is made again to FIG. 3. Impactor 15 is located at the distal tip of crossing device 1, protruding at its rest position, from the distal end of device 1 distal section 11. Impactor 15 is preferably, but not necessarily, made from a hard metal such as stainless steel. Impactor 15 is connected to an inner tube 17 of the device. A stopper 16 is bonded or otherwise attached to the distal shaft portion 11 to limit backwards movement of distal biasing device 14. Tube 17 is capable of sliding inside the distal shaft portion 11, and is preferably, but not necessarily, made from a metal tube, such as a stainless steel hypotube.

Tube 17 is preferably welded or otherwise attached to a metal anchor 18, which may be made from a hard bent metal wire. A flexible link, cord or wire 19 (the terms being used interchangeably), which may be made from flexible polymer like Teflon or silk, is tied or otherwise attached to metal anchor 18. Other cord anchoring mechanisms can be used. Pulling cord 19 causes tube 17 with impactor 15 to move backwards, storing potential energy in spring 14 through the backwards movement. Releasing cord 19 releases distal biasing device 14, allowing quick forward movement of impactor 15 towards plaque 4 and proximal plaque cap 5 (FIGS. 4A-4B).

The distal edge of distal shaft portion 11 includes a bulge or step that limits the forward movement of impactor 15, thereby preventing long and uncontrolled displacement of impactor 15 into plaque 4. Protrusion of crossing device 1 led by impactor 15 into and through the plaque is done in small multiple steps, limited in length by the small protrusion of impactor 15 from distal portion 11. Such steps are preferably in the range of 0.5 mm to 3.0 mm, and more preferably about 1.0 mm. Multiple steps forward means many distal biasing device activations in order to penetrate long occlusions.

Distal biasing device 14 can be pre-loaded (e.g., compressed) by impactor 15, as is now explained. Since shaft 10 and distal portion 11 are preferably inserted percutaneously, the diameter of the shaft and distal portion are relatively small, such as in the range of 1.5-2.5 mm. Larger diameters require a cut-down incision to insert the device. Using such a small diameter shaft and distal portion requires using very small distal biasing devices. Such small springs needs to be squeezed for a long displacement to store enough energy for significant impact when released. Long displacements require long springs and a long stiff distal portion, which may limit the device 1 pass through bent and curved blood vessels. It also requires a long pulling maneuver of cord 19. To overcome this spring size limitation, distal biasing device 14 is preferably pre-loaded. Such a preloaded spring stores energy even when cord 19 is not pulled at all. When cord 19 is pulled back, the added energy is sufficiently great to allow significant impact on plaque 4, and especially on the occlusion proximal cap 5, by impactor 15 that is attached to spring 14 distal end.

For example: the force applied by spring is $F=kX$, when F is Force, X is displacement, and k is the spring constant that related to its size and material.

Potential energy stored in spring $E=kX^2/2$. If the spring displacement X=1 cm from rest, the impact energy will be E=0.5 k. In contrast, if the spring is preloaded to a displacement of 5 cm, and then moves 1 cm from 5 cm to 6 cm, the energy released for the impact is $E=\frac{1}{2}(6^2k)-\frac{1}{2}(5^2k)$, meaning E=5.5 k. Thus, the pre-load on the spring can have an order of magnitude greater impact than a spring that is not pre-loaded.

Figure 5:
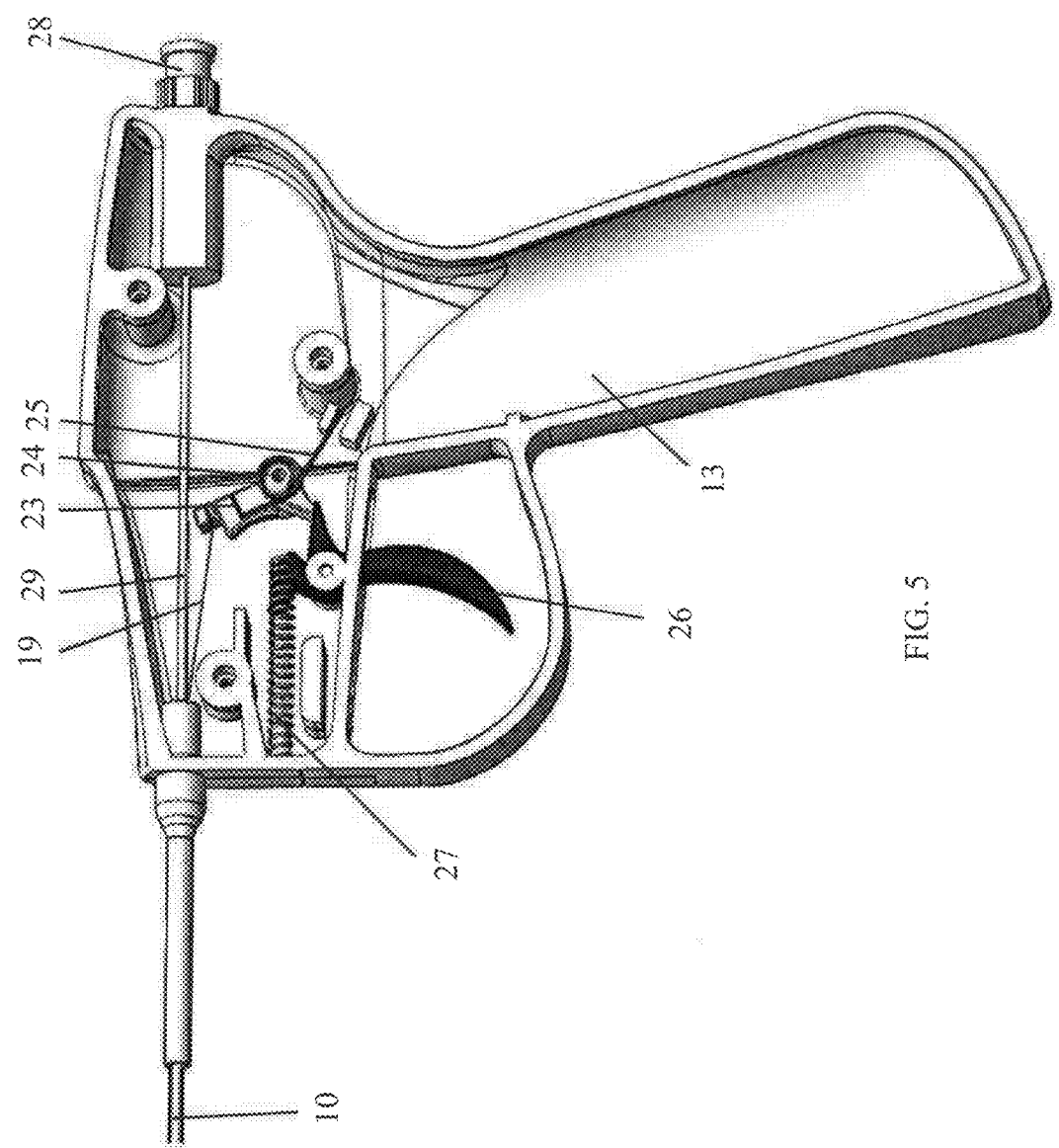
FIG. 5 is a cross-section schematic illustration of an embodiment of the handle of the device of the invention.

Reference is now made to FIG. 5. Crossing device 1 includes a small thin flexible tube 29 having a lumen suitable for the guidewire to pass through. Tube 29 extends through handle 13 and shaft 10, including shaft proximal portion 12 and distal portion 11.

Cord 19 is tied or otherwise attached to a rotating member 23 that can rotate around a pivot, e.g., pin 24. A biasing device, such as a torsion spring 25, applies a biasing force that works against the pivoting or swivel of rotating member 23 and against the pulling of cord 19. Rotating member 23 is rotated by pulling trigger 26 against the force of trigger return spring 27 and torsion spring 25. (For example, a trigger tail of the trigger may push against member 23.)

Handle 13 includes a luer port 28 in communication with the thin guidewire tube 29 and the guidewire lumen.

In another embodiment of the invention, the pulling mechanism for cord 19 includes an additional pulling spring 30 positioned between cord 19 and rotating member 23. Spring 30 may compensate for any pulling movement variations when the device shaft bends inside the blood vessels. Such bending might shorten the cord path or reduce its tension, so that a different pulling length is needed to fully withdraw distal biasing device 14 as opposed to when shaft 10 is straight; such bending may reduce the energy stored and the potential impact. The compensating spring 30 is significantly stiffer then distal biasing device 14 and in this design the rotation of member 23 produces a larger displacement then needed to fully pull distal biasing device 14. Whenever cord 19 is tight, both springs will move, first distal biasing device 14 is fully squeezed and afterwards compensating spring 30 is elongated, until trigger 26 completes a full backwards movement. When cord 19 is loose due to the shaft 10 bending, the cord pulling will just pull impactor 15 and squeeze distal biasing device 14 and then only slightly pull the compensating spring 30 when trigger 26 completes its backwards movement.

Other handle mechanisms can be used to activate impactor 15.

Figure 6:
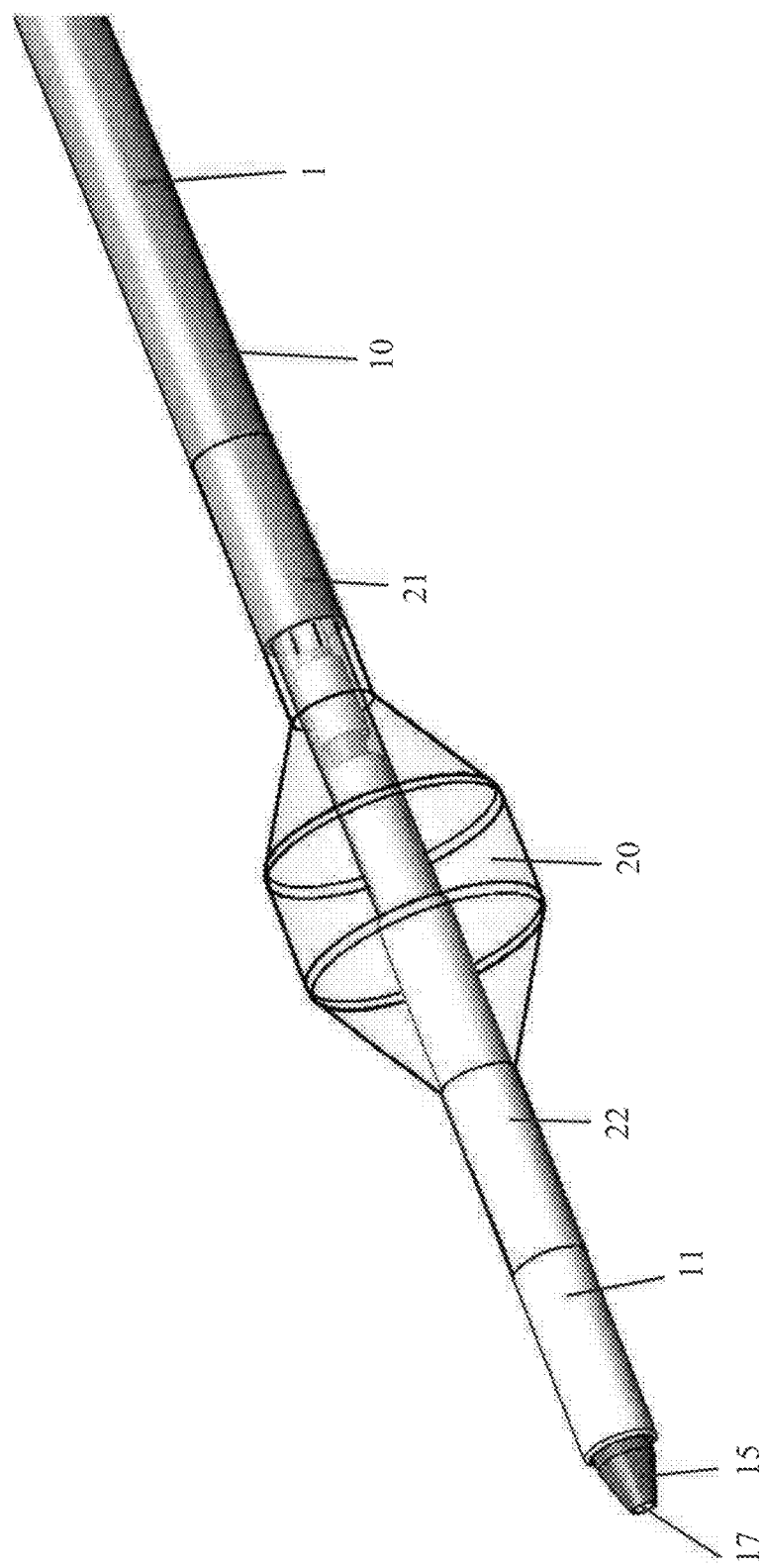
FIG. 6 is a schematic illustration of an embodiment of the crossing device of the invention having centering balloon.
Figure 7:
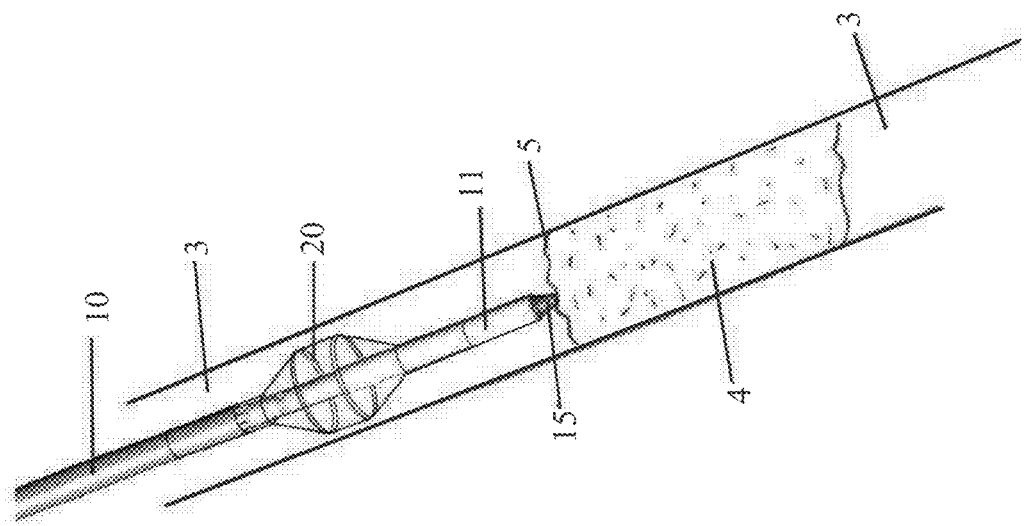
FIG. 7 is a schematic illustration of an embodiment of the distal section of the crossing device of the invention with centering balloon, inside blood vessel with total occlusion.
Figure 8:
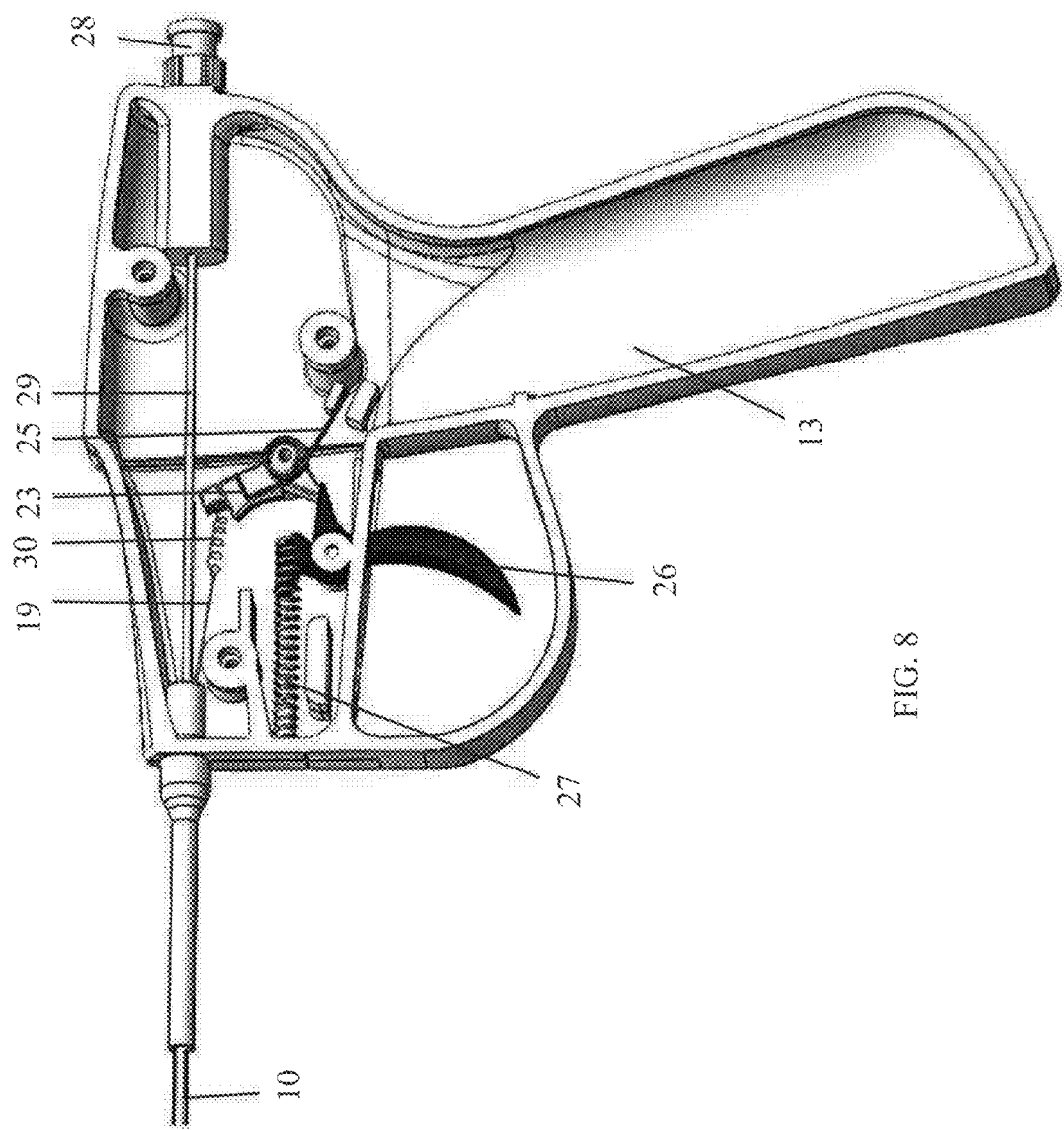
FIG. 8 is another cross-section schematic illustration of an embodiment of the handle of the device of the invention with compensating spring.

Reference is now made to FIGS. 6 and 7. In another embodiment of the present invention, a centering balloon 20 is added to the crossing device 1, positioned just proximally to the device distal tip. Balloon 20 is preferably slightly smaller than the blood vessel lumen, not to disturb the device advancement through the occlusion, but rather just to aim the device tip to the center of the occlusion before applying the impact (as in FIG. 7). Balloon 20 directs the impacts of impactor 15 towards the proximal cap 5 and plaque 4 center area, preventing the impact from being directed to blood vessel 3 walls.

Centering balloon 20 can be non-compliant or semi-compliant, made from materials known in the art for medical balloons, such as polyurethane, PEBAX or nylon. Balloon 20 preferably has a proximal neck 21 bonded or otherwise attached to shaft 10, and a distal neck 22 bonded or otherwise attached to the distal portion 11 of shaft 10. Separate inflation and deflation lumens may be provided in shaft 10, as well as inflation and deflation ports in or near handle 13 (not shown) to activate centering balloon 20.

What is claimed is:

1. A crossing device comprising:
    a shaft having a distal portion and a proximal portion;
    a handle with an activating mechanism attached to said proximal shaft portion; and
    an impactor fixedly connected to a tube and positioned at said distal portion, said impactor being biased by a distal biasing device which abuts against a proximal face of said impactor, and said tube being arranged to slide inside said distal portion, wherein said tube is coupled to said activating mechanism, said distal biasing device operative to store energy and release energy as an impact force through said impactor sufficient to penetrate or break through hard plaque in blood vessels;
    and wherein fixed connection of said impactor to said tube is independent of any connection of said impactor or said tube with respect to said shaft and wherein said distal biasing device is external to said impactor, and wherein said tube is coupled to said activating mechanism with a cord and said cord is attached to a rotating member arranged to rotate around a pivot.

2. The crossing device according to claim 1, further comprising a stopper at said distal portion arranged to limit backwards movement of said distal biasing device.

3. The crossing device according to claim 1, wherein said distal portion includes a bulge or step that limits forward movement of said impactor.

4. The crossing device according to claim 1, wherein said distal biasing device is pre-loaded by said impactor.

5. The crossing device according to claim 1, further comprising a flexible tube having a lumen suitable for a guidewire to pass through, said flexible tube extending through said handle and said shaft.

6. The crossing device according to claim 1, wherein a biasing device is operative to apply a biasing force that works against pivoting of said rotating member and against pulling of said cord.

7. The crossing device according to claim 1, wherein said rotating member is rotated by said activating mechanism.

8. The crossing device according to claim 1, wherein said handle comprises a luer port in communication with a guidewire tube.

9. The crossing device according to claim 1, further comprising an additional pulling spring positioned between said cord and said rotating member.

10. The crossing device according to claim 1, further comprising a centering balloon positioned proximally to a distal tip of the device.

* * * * *